United States Patent
Sako

(10) Patent No.: US 7,119,841 B1
(45) Date of Patent: Oct. 10, 2006

(54) IMAGE PROCESSING APPARATUS METHOD AND STORAGE MEDIUM THEREFOR

(75) Inventor: Tsukasa Sako, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/552,590

(22) Filed: Apr. 19, 2000

(30) Foreign Application Priority Data

Apr. 27, 1999 (JP) .................. 11-119630

(51) Int. Cl.
*H04N 5/222* (2006.01)
*H04N 5/76* (2006.01)
*H05G 1/28* (2006.01)

(52) U.S. Cl. ............... 348/333.05; 348/231.3; 378/165

(58) Field of Classification Search ........... 348/207.99, 348/211.99, 571, 222.1, 575, 584–589, 600, 348/333.01, 333.05, 231.3; 345/721, 629; 382/254; 600/409, 443, 160; 351/206, 221; 364/413.22; 378/98.5, 116, 165
See application file for complete search history.

(56) References Cited

U.S. PATENT DOCUMENTS

| | | | | |
|---|---|---|---|---|
| 5,384,862 A | * | 1/1995 | Echerer et al. ............. | 382/132 |
| 5,440,607 A | * | 8/1995 | Nakaya ...................... | 378/98.2 |
| 5,616,930 A | * | 4/1997 | Janssens et al. ............ | 250/584 |
| 5,640,628 A | * | 6/1997 | Yoshida ...................... | 396/311 |
| 5,807,256 A | * | 9/1998 | Taguchi et al. ............. | 600/425 |
| 6,155,683 A | * | 12/2000 | Hanaki et al. .............. | 351/206 |
| 6,282,513 B1 | * | 8/2001 | Strawder ....................... | 705/2 |
| 6,359,628 B1 | * | 3/2002 | Buytaert ..................... | 345/619 |
| 6,501,827 B1 | * | 12/2002 | Takasawa ................... | 378/116 |
| 6,522,354 B1 | * | 2/2003 | Kawamura et al. ...... | 348/231.2 |
| 6,593,938 B1 | * | 7/2003 | Sakata et al. .............. | 345/629 |
| 6,657,667 B1 | * | 12/2003 | Anderson ............. | 348/333.12 |

FOREIGN PATENT DOCUMENTS

| | | |
|---|---|---|
| JP | 01-242035 | 9/1989 |
| JP | 04-132542 | 5/1992 |
| JP | 04-336053 | 11/1992 |

* cited by examiner

*Primary Examiner*—Tuan Ho
*Assistant Examiner*—Kelly L. Jerabek
(74) *Attorney, Agent, or Firm*—Fitzpatrick, Cella, Harper & Scinto

(57) ABSTRACT

From among a group of taken images, an image suitable for inspection is identifiably displayed and can be arbitrarily selected. Also an image may be re-taken as a result of an instruction for re-taking the image and also displayed on a display. Images already taken prior to the re-taking of the image are displayed with a character or symbol, such as a cross mark, for easy identification by the operator. Also, the operator may arbitrarily select an image from the re-taken image and the already taken images.

27 Claims, 11 Drawing Sheets

IMAGE PROCESSING APPARATUS METHOD AND STORAGE MEDIUM THEREFOR

BACKGROUND OF THE INVENTION

Field of the Invention

The present invention relates to an image processing apparatus capable of image taking, a method and a storage medium therefor.

In the medical field, the diagnosis with image has meant observation of the image recorded on the X-ray film on the film viewing light box (schaukasten).

However, the ordinary X-ray film is so designed as to have a high image contrast in an easily observable density range of about 1.0 to 1.5 D in order to facilitate the observation of the body part to be diagnosed, so that even a slight aberration in the image taking condition results in an overexposure or an underexposure, thus detrimentally affecting the diagnosis by image reading.

Particularly in case of divided image taking, the image contrast and object of diagnosis are different respectively for the diagnosed parts recorded in the divided areas on the film, so that various efforts have been made for obtaining the desired images.

On the other hand, with the recent progress in computer technology, computerization has been introduced also in the medical field. This trend is evident also in the diagnosis with image, including remarkable progress in the computed tomography (CT), ultrasonic diagnostic equipment and equipment for radio isotope diagnosis. Further, there has been developed a concept "comprehensive diagnostic imaging (or integrated image diagnosis)" of connecting various diagnostic equipment with a computer and integrally diagnosing the images of different modalities.

However, the image on the X-ray image is basically an analog image and cannot be satisfactorily incorporated in the integrated image diagnosis, thus retarding the computerization in the image diagnosis field, though it is most frequently utilized and considered most important in the image diagnosis.

Nevertheless, the X-ray image taking with a solid-state image taking device is recently developed, and the image taking with the computerized digital X-ray image reading apparatus has gradually started in the X-ray image field. Such image taking method is featured in that the image can be confirmed immediately after the image taking.

In such digital X-ray image taking, the blur in the taken image caused by the movement of the subject patient can be found immediately after the image taking operation, so that there is frequency executed the image re-taking operation, which is not often executed in the conventional analog image taking. In such case, regardless of the number of the image re-taking operations, the image finally outputted from the apparatus has to be arbitrarily selected among thus taken images.

Also the last taken image is not necessarily the best image in the final judgment, and there may be encountered a situation where, despite of the image re-taking, the image prior to the re-taking is better. It has therefore been desired to meet such requirements.

SUMMARY OF THE INVENTION

In an embodiment of the present invention, there is provided an image processing apparatus comprising designation means for designating the image taking conditions relating to the image taking, image taking means for taking an image under the image taking conditions designated by the designation means, storage means for storing the image, taken by the image taking means, as an already taken image, discrimination means for discriminating whether the storage means contains an already taken image taken under the same image taking condition, and output control means for effecting control in such a manner, in case the discrimination means identifies that an already taken image taken under the same image taking condition is present, as to the later taken image as the re-taken image.

DESCRIPTION OF THE PREFERRED EMBODIMENTS

In the following there will be explained an X-ray image taking apparatus.

Figure 1:
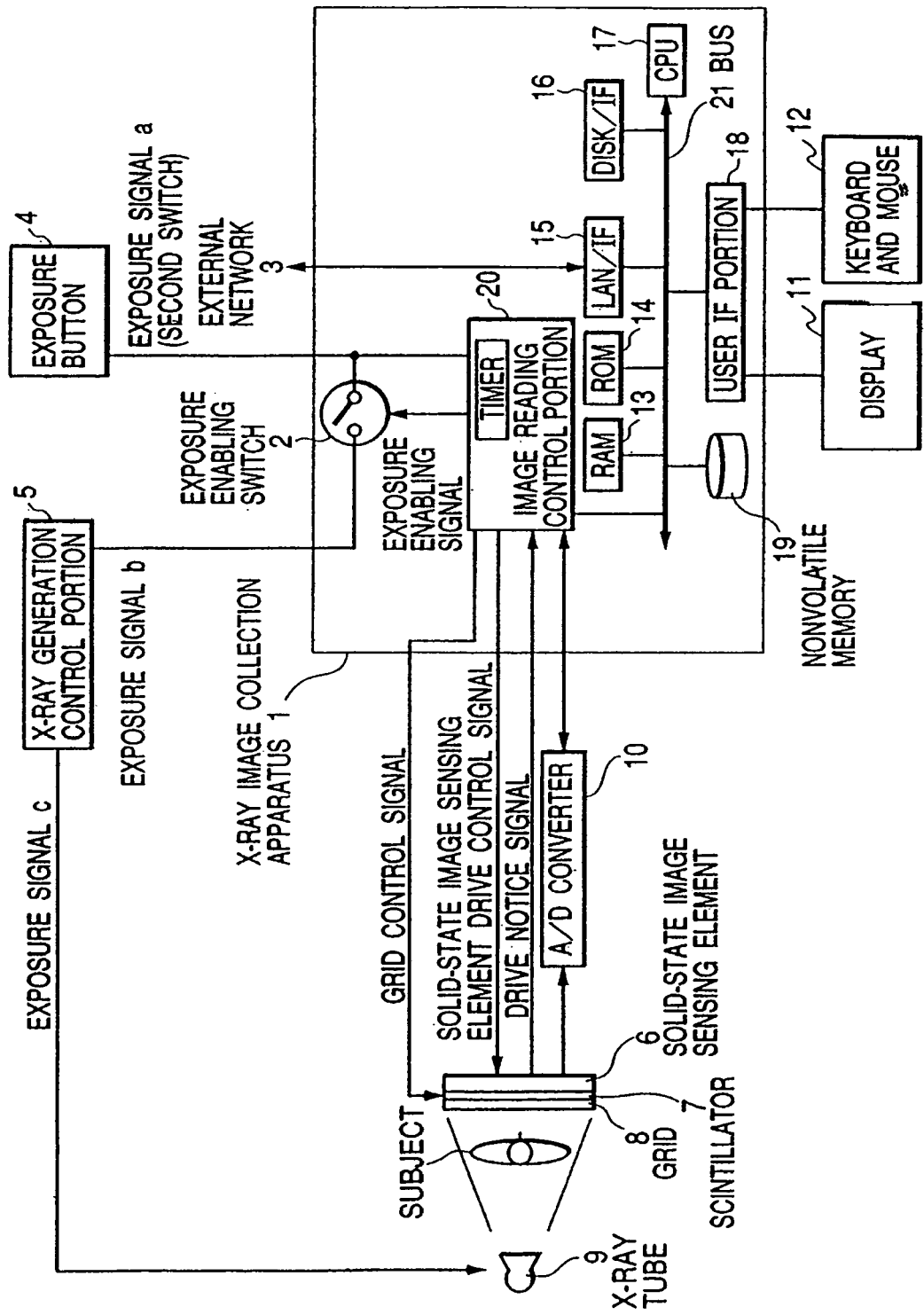
FIG. 1 is a block diagram showing the configuration of an X-ray image collection apparatus.

FIG. 1 is a block diagram showing the configuration of the X-ray image taking (sensing) apparatus.

The X-ray image collection apparatus 1 receives the ordering information from an external network 3. The present embodiment has two modes, namely a mode of automatically entering an image taking start procedure simultaneously with the reception of the ordering information and another mode of entering the image taking start procedure with the received ordering information through a user interface. These modes will not be explained here since they will be explained later with reference to FIG. 2.

At first the operator places a subject to be taken between a solid-state image taking element 6 and an X-ray tube 9. Then a part setting button, for setting the part to be taken, assumes a state selected according to the ordering information. Subsequently, based on a solid-state image taking element drive control signal, the system applies a voltage to the solid-state image taking element thereby preparing the solid-state image taking element for image input.

Also a grid operating speed parameter is adjusted. An exposure button 4 serves as a trigger for generating the X-ray. An exposure signal "a" generated by the exposure button 4 is entered into an image reading control portion 20 of the image collection apparatus 1. The image reading control portion 20, after confirming whether the solid-state image taking element 6 is in a state of forming an image upon receiving the X-ray by the state of a drive information signal, generates an exposure enabling signal. The exposure permission signal turns on an exposure enabling switch 2, thereby passing the exposure signal "a" as an exposure signal "b". The switch employed for this purpose is called a second switch of the exposure button. The exposure signal "b" is transferred to an X-ray generation control portion 5.

As soon as the preparation for X-ray exposure is completed, such as a grid 8 starts movement and reaches an optimum speed, the X-ray generation control portion 5 generates an exposure signal c to generate X-ray from the X-ray tube 9. After the exposure, the transmitted X-ray is entered, through the grid 8 and a scintillator 7, as an image into the solid-state image taking element 6. This image is read and digitized in an A/D converter 10 and transferred to an image reading control portion 20.

The image reading control portion 20 is controlled by a CPU 17, which is also connected, through a bus 21, to a RAM 13, a ROM 14, a LAN/IF 15, a DISK/IF 16, a control panel, a non-volatile storage device 19 and a user IF 18. The non-volatile storage device 19 in the present embodiment is composed of a hard disk. The user IF 18 is provided with a display 11 and a keyboard/mouse 12 for interfacing with the user. Naturally there may be employed a touch panel. The image transferred to the image reading control portion 20 is stored in the RAM 13 and is subjected to various processing to be explained later in the CPU.

Figure 2:
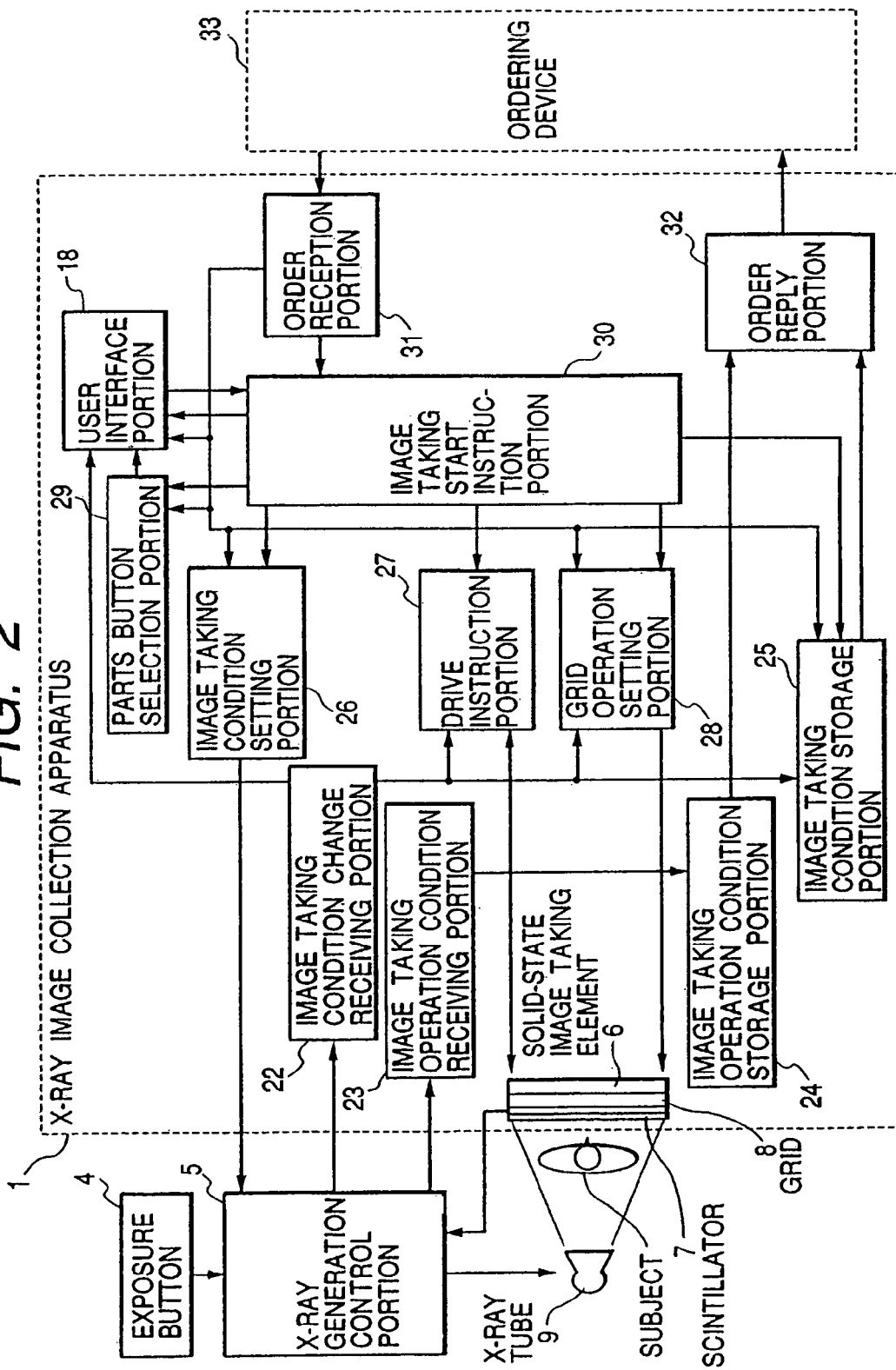
FIG. 2 is a view showing the functional configuration of the X-ray image collection apparatus.

FIG. 2 is a view showing the functional configuration of the X-ray image collection apparatus.

Order information from the ordering device 33 is received by an order reception portion 31. Upon reception of the order, the arrival of the order is informed to an image taking start instruction portion 30. In the present embodiment, the image taking start instruction portion 30 has two modes, namely a mode of automatically entering the image taking start procedure simultaneously with the reception and a mode of entering the image taking start procedure with the received ordering information through a user interface. In the latter mode the user interface portion 18 displays a list of the received order and there is provided an advantage that the order can be selected from such list. In such case, prior to the reception of the order information, a request is given to the ordering device 33 for transmitting the list of orders.

In either case, when the image taking start procedure is started, the order is interpreted in the order reception portion 31 and the personal information of the order, such as the name and birth date of the subject to be inspected, is transferred from the order reception portion 31 to the user interface 18 together with the instruction for starting the image taking. The user interface 18 displays the name of the subject whereby the subject to be inspected can be confirmed.

At the same time, the part information, a $1^{st}$ body part ordered for inspection, is transferred from the order reception portion 31 to a parts button selection portion 29 together with the instruction for starting the image taking. Thus, the parts button selection portion 29 enables a part button of the corresponding part for selection. Also the user interface 18 displays the image taking condition according to the ordered image taking information. As will be clarified in the following description, as soon as the image taking of the ordered $1^{st}$ part is completed, the image taking procedure is started according to the part information of a $2^{nd}$ body part.

Then the image taking condition is transferred from the order reception portion 31 to an image taking condition setting portion 26, together with the instruction for starting the image taking. The image taking condition setting portion 26 sets the conditions of the X-ray tube, such as the tube voltage and the focus size, in the X-ray generation control portion 5 according to the ordered image taking condition.

Then the image taking condition is transferred from the order reception portion 31 to a drive instruction portion 27 together with the instruction for starting the image taking. The drive instruction portion 27 applies a voltage to the solid-state image taking element 6 thereby shifting it to a driven state. The driven state is not an image taking state but a state in which the voltage required for image collection is not applied in order to extend the service life of the solid-state image taking element 6. The driven state expires after 1 minute if the image taking procedure is not executed, and returns to a non-driven state.

Then the image taking condition is transferred from the order reception portion 31 to a grid operation setting portion 28 together with the instruction for starting the image taking. The grid operation setting portion 28 determines the grid speed parameter, preset depending for example on the information of the body part for which the image taking is to be executed. For example, the grid speed is lowered or elevated respectively for a part requiring a long exposure time and a part requiring a short exposure time.

Then the image taking condition is transferred from the order reception portion 31 to an image taking operation condition storage portion 24, together with the instruction for starting the image taking. In order to manage the history of the image taking information, the storage is made in the RAM and the hard disk of the system.

In the following there will be explained a case where the tube setting is changed in the X-ray generation control portion 5.

In the present embodiment, the operator can arbitrarily set, in the X-ray generation control portion 5, a condition such as the tube voltage or the focus size different from the ordered image taking condition, according to the health state of the subject. In such case, the X-ray image collection apparatus 1 accepts the change of the image taking condition from an image taking condition change receiving portion 22. The drive instruction portion, the grid operation setting portion 28 and the image taking condition storage portion 25 execute the above-described procedures again since the image taking condition is reset. Also the user interface 18 displayed the changed image taking condition.

In response to the depression of the exposure button 4, the X-ray tube 9 executes the exposure. The data flow in this procedure will not be explained since it is already illustrated in FIG. 1, but a signal is sent to the X-ray image collection apparatus 1 to send an operation signal to the grid and the solid-state image taking element 6.

In response to the depression of the exposure button 4 by the operator, the X-ray is generated to execute the image taking. Thereafter, the image taking operation condition, such as the image taking time and the mAs value, is generated by the X-ray generation control portion 5, and is received by the image operation condition receiving portion 23 and transferred to an image taking operation condition storage portion 24. The storage is made in the RAM and the hard disk of the system in order to manage the history of the image taking operation.

When the image taking sequence is completed, a next image taking sequence is started to repeat the above-described procedures.

When the inspection consisting of single or plural image taking sequence is completed, the information in the image taking condition storage portion 24 and the image taking operation condition storage portion 25 is transmitted to an order reply portion 32, which informs the completion of the inspection according to a communication protocol determined in advance with the ordering device 33. In this operation, there are transmitted the image taking condition and the image taking operation condition under which the image taking was executed.

One of the features of the present embodiment lies in a fact that the X-ray generation control portion 5 is provided for setting the solid-state image taking element 6 in the driven state. Therefore, even if the image taking element is shifted to the non-driven state upon expiration of 1 minute, it can be reset to the driven state by an instruction for changing the parameter from the X-ray generation control portion 5. Therefore, the instruction for change is given from the X-ray generation control portion 5 even if the parameter remains the same before and after the change. This function allows the operator to execute the image taking operation even without looking at the display on the X-ray image collection apparatus 1.

Figure 3:
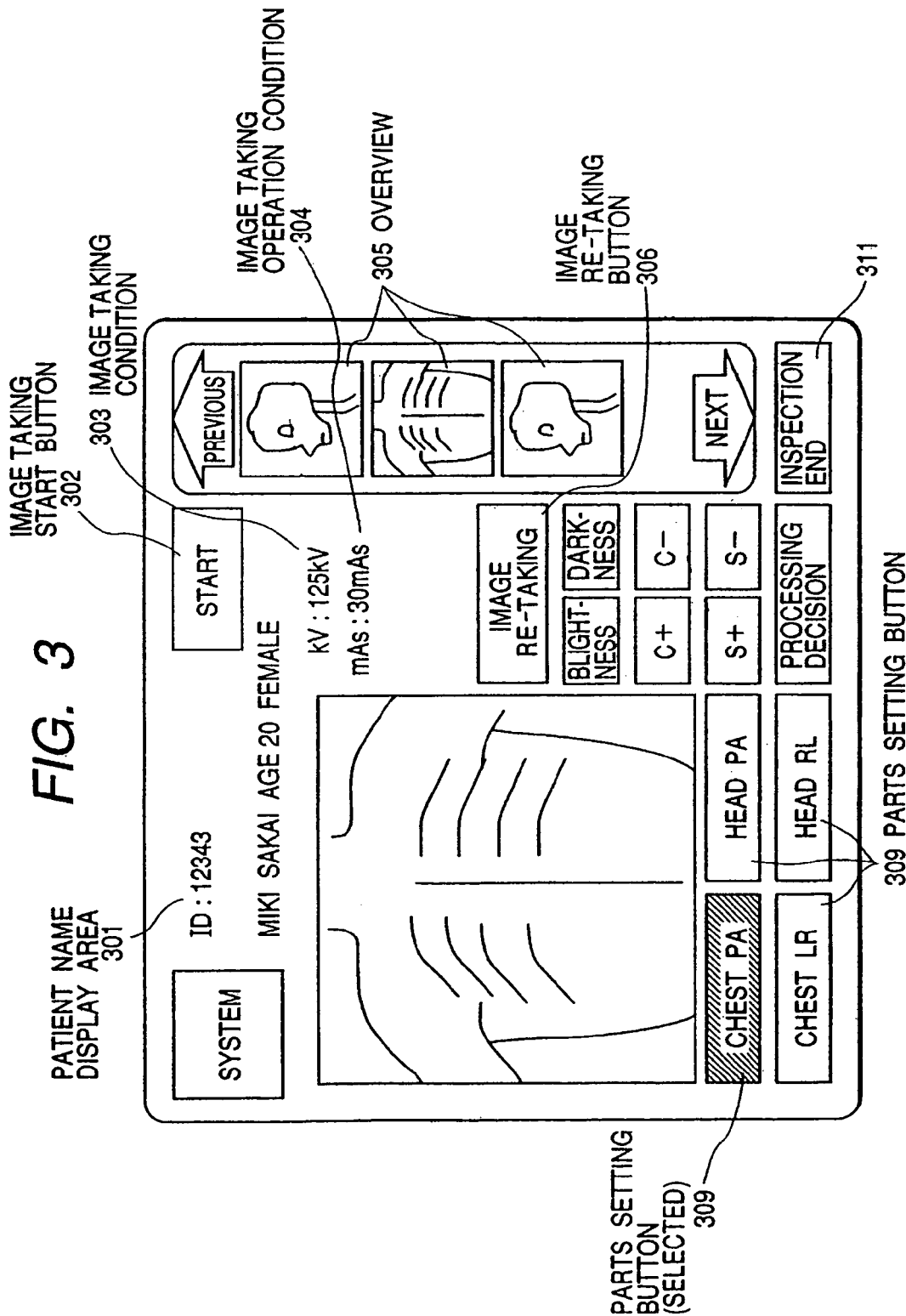
FIG. 3 is a view showing an example of the image on a display portion 11 in an embodiment of the present invention.

FIG. 3 shows an example of the display of a display portion 11 in the present embodiment.

At the image taking operation, the operator depresses an image taking start button 302 to request that the ordering device 33 transmits the order list, whereby the received order list is displayed to enable selection of an order therefrom. In a case where the transmission of the order list is not requested, and if the order is transmitted from the ordering device 33 to the X-ray image collection apparatus 1, the image taking start procedure is initiated according to the received ordering information. When the image taking procedure is started, a "chest PA" button 310 indicating the initial image taking part is rendered selectable as illustrated. Also as the image taking condition 303, there is displayed a tube voltage of 125 kV. This value can be changed in the X-ray generation control portion 5, and is changed on a real-time basis according to the change in the X-ray generation control portion 5. The image taking operation is thereafter executed, and the image taking operation condition 304 of 30 mAs is displayed on the user interface. When all the image taking operations are executed, the inspection is terminated either by the depression of an inspection end button 311 or automatically by a time-out. Upon completion of the inspection, the image taking information and the image taking operation information are returned to the ordering device 33 as explained in the foregoing. Also the collected images are externally transferred through the network.

In the foregoing there has been explained the method collecting the images according to the ordering information, by image taking operation in succession on the designated parts under pre-designated conditions, but the image taking may not be successful in one operation, mostly because of the movement of the subject. The movement of the subject causes a blur in the obtained image, eventually causing a difficulty in the diagnosis.

However, in case of image taking again, the re-taking is not required for all the images collected prior to the re-taking according to the order from the HIS (hospital information system) but is often required for a body part under the designated condition. This invention is to meet such requirement.

Figure 4:
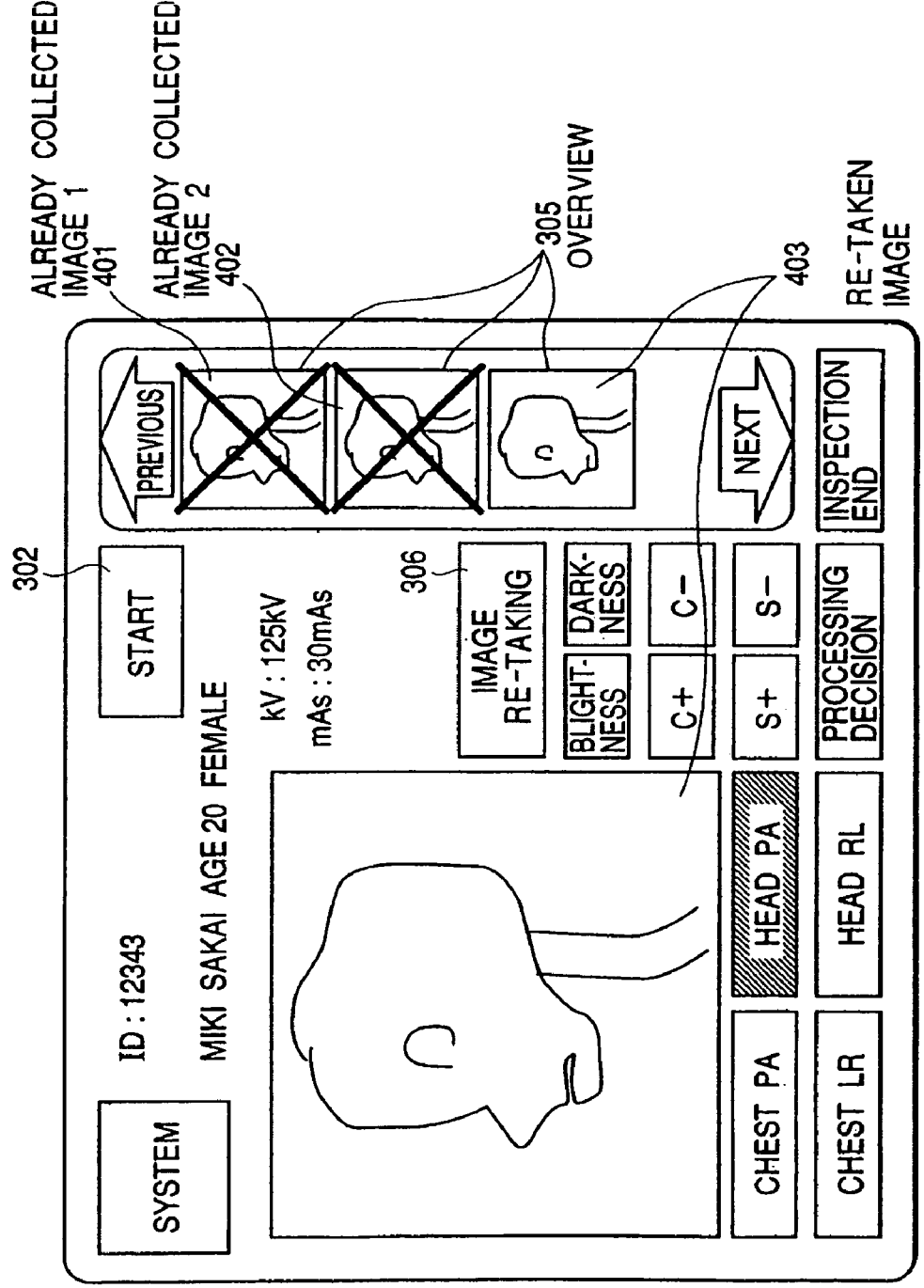
FIG. 4 is a view showing the state of the display portion 11 after image re-taking.

FIG. 4 is a view showing the state of the display portion 11 after image re-taking.

In case the image re-taking becomes necessary because of an image blur at the image taking of the head portion, an image re-taking button 306 is depressed, whereby there is reached a state ready for image re-taking. In such case, there is usually used the same image taking condition, but the image taking condition may also be changed if the operator judges that the image taking cannot be properly executed under the same image taking condition, for example because of the body size of the subject.

Then the exposure button 4 is depressed to execute the image re-taking, whereupon the re-taken image is displayed as illustrated. The previous image, which is now regarded as an already collected image because of the image re-taking, is to be replaced by the re-taken image in the default condition, and is therefore displayed with a cross mark thereon. FIG. 4 shows a case where the image re-taking is executed twice.

The operator may execute the image re-taking plural times, but the image transferred externally as the ordered image is not necessarily the one taken last. When the already collected image 1 in FIG. 4 is selected with the mouse, such image becomes the representative image and the cross mark is removed from such image while the last taken image is displayed with a cross mark. In this manner the selected image alone becomes the image constituting the result of the order while other images are regarded as failure.

Also the taken images are stored in the non-volatile storage device shown in FIG. 1 even after the image re-taking, and can be read and transferred in case there is required an image other than the image constituting the result of the order.

Figure 5:
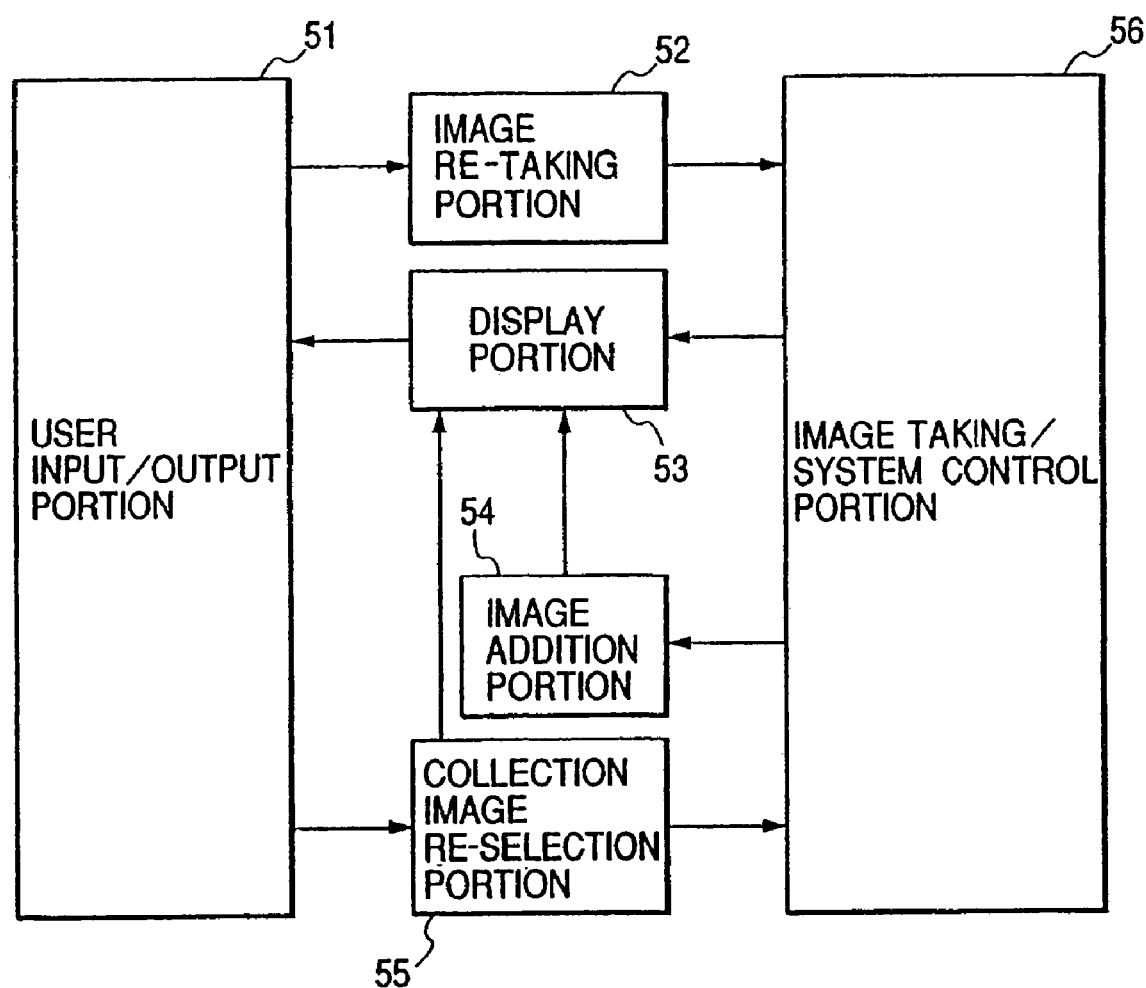
FIG. 5 is a view showing the functional configuration relating to the image re-taking operation of the X-ray image collection apparatus.

FIG. 5 is a view showing the functional configuration relating to the image re-taking process of the X-ray image collection apparatus.

When the operator depresses the image re-taking button 306 for executing the image re-taking, a notice is given to a user input/output portion 51 and further from an image re-taking portion 52 to an image taking/system control portion 56 controlling the image taking operation. The image taking/system control portion 56 prepares for the image taking, and the image taking operation is executed when the operator depressed the exposure button (not shown in FIG. 5).

Subsequently the taken image is transferred through an image addition portion 54 to a display portion 53, which thus displays the image on the display through the user input/output portion 51. (Image addition means adding an image to an overview list.)

When the user re-selects, on the user input/output portion 51, the representative image from the images obtained by image re-taking, a notice is given to a collection image re-selection portion 55 and further to the display portion 53 and the image re-taking/system control portion 56. The display portion 53 executes erasure and setting of the cross marks, while the image taking/system control portion 56 maintains the representative image, and transfers the representative image only to the network when the inspection is terminated.

In the following there will be explained the image re-taking process, with reference to flow charts shown in FIGS. 11 to 13.

Figure 11:
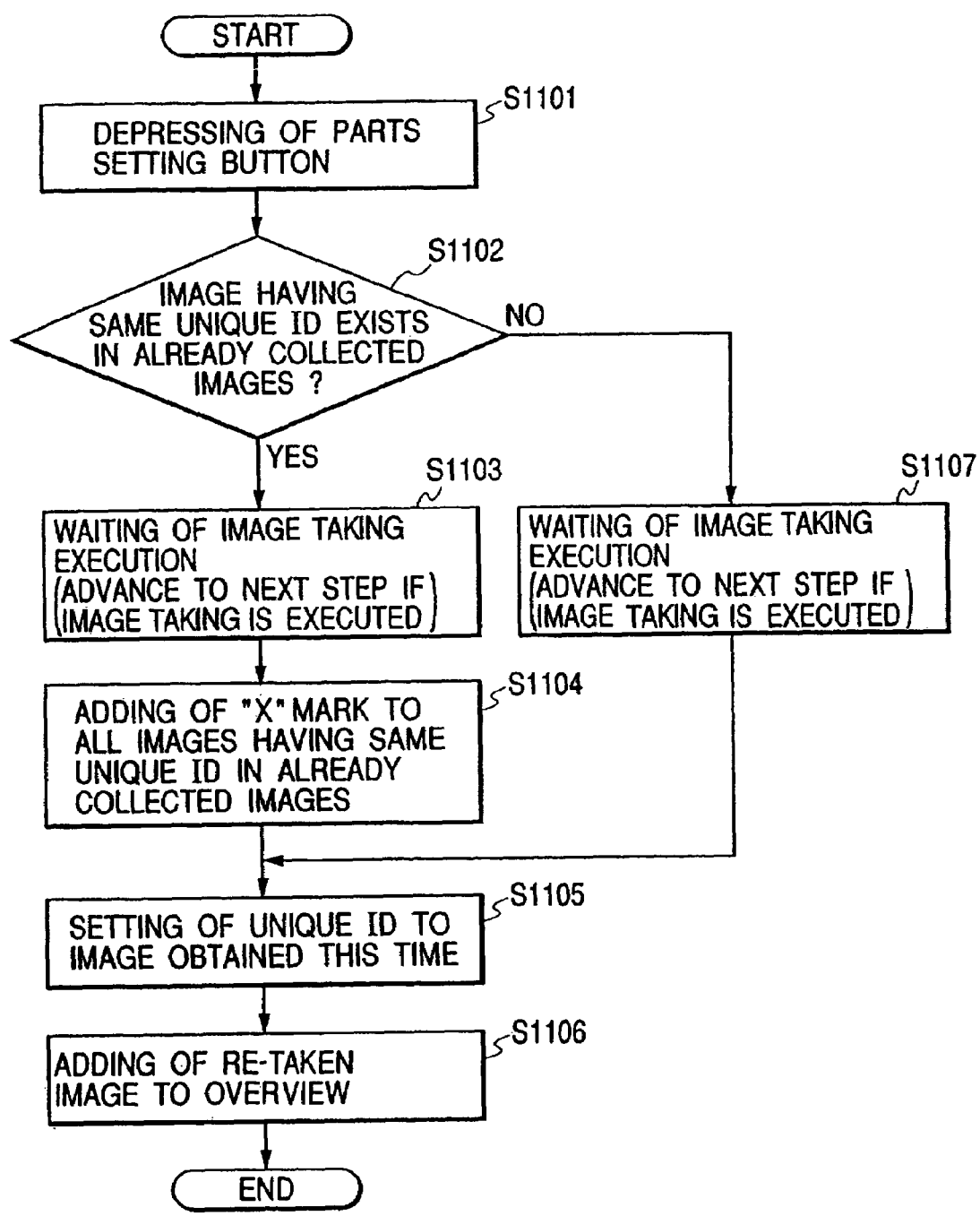
FIG. 11 is a flow chart of an image re-taking process by a part setting button 309.

FIG. 11 is a flow chart of the image re-taking process by the actuation of the part setting button 309.

A step S1101 discriminates whether the part setting button 309 has been depressed, and, if depressed, the sequence proceeds to a step S1102. The step S1102 discriminates whether an image with the same unique ID (Patent Name Display Area 301) is present in the already taken images, namely the already collected images, and the sequence proceeds to a step S1103 or S1107, respectively, such that the image is present or absent. The unique ID (Patent Name Display Area 301) is information for specifying the image taking information such as the subject name, body part to be taken, image taking direction, image taking condition, etc.

A step S1103 enters a stand-by state for executing the image taking operation, and, when the image taking operation is executed, the sequence proceeds to a step S1104. Also a step S1107 enters a stand-by state for executing the image taking operation, and, when the image taking operation is executed, the sequence proceeds to a step S1105.

A step S1104 attaches cross marks on all the images of the same unique ID in the already collected images. In this state, the already collected images 1 (401) and 2 (402) are displayed with the cross marks, as shown in FIG. 4. Then a step S1105 sets, on the last taken image, namely the re-taken image 403 in FIG. 4, a unique ID, same as that of the already collected images 1 (401) and 2 (402). Then a step S1106 displays the re-taken image in an overview 305 whereupon the image re-taking process is terminated.

In the following there will be explained, with reference to FIG. 12, the image re-taking process when the image re-taking is instructed.

Figure 12:
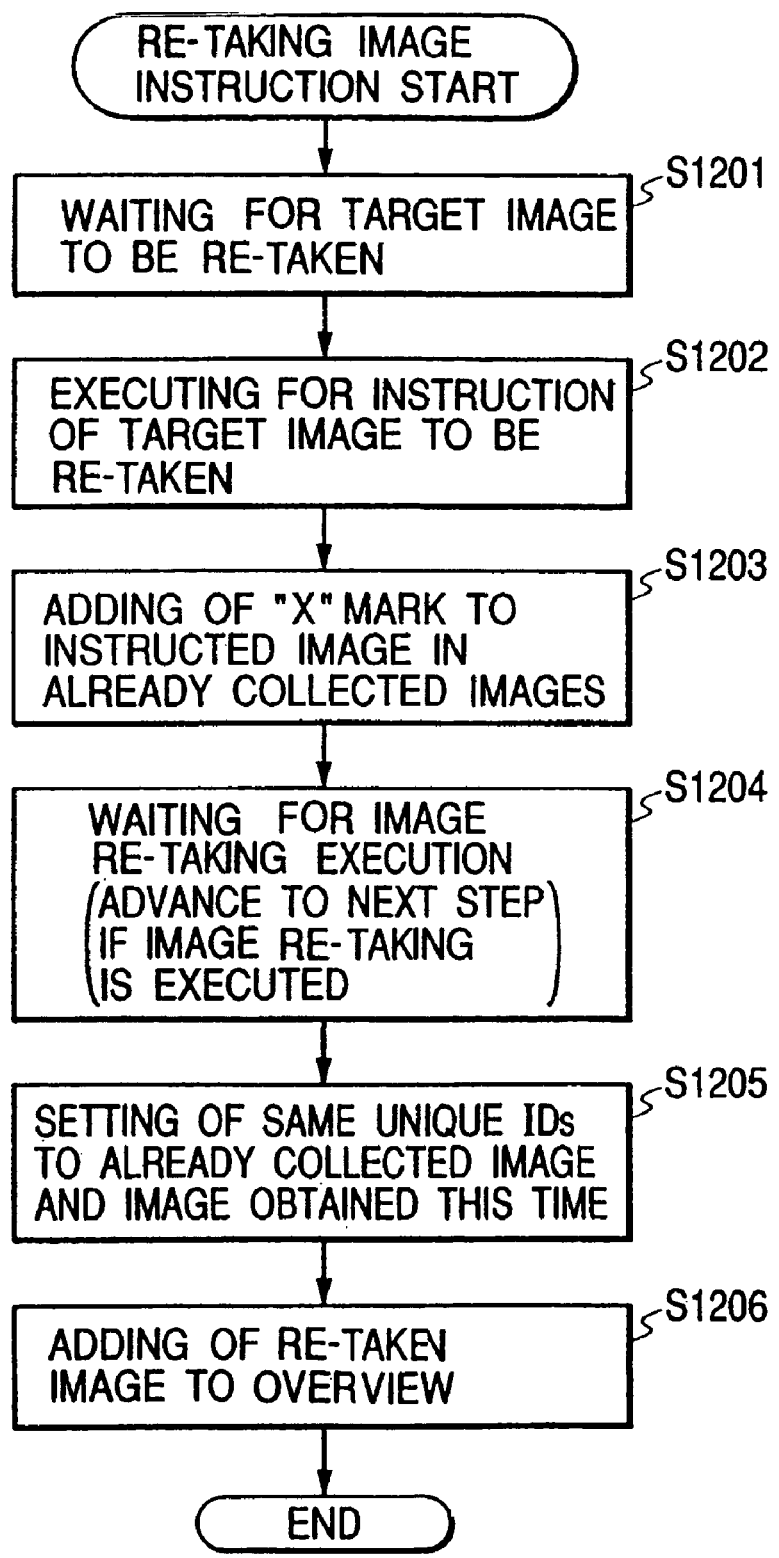
FIG. 12 is a flow chart of an image re-taking process in case an image-retaking is designated.

The sequence of FIG. 12 is initiated when the image re-taking is instructed for example by the image re-taking button 306. A step S1201 enters a state for waiting for a re-taking object image to be re-taken, and, when the re-taking object image is displayed on the display portion 11, the sequence proceeds to a step S1202. A step S1202 discriminates whether the re-taking object image is designated among the object images displayed in the step S1201, and, if designated, the sequence proceeds to a step S1203. A step S1203 attaches a cross mark to the designated re-taking object image, namely the already collected image. This state is illustrated in FIG. 4.

Then a step S1204 enters a stand-by state for executing the image re-taking operation. When the image re-taking operation is executed, the sequence proceeds to a step S1205. A step S1205 sets a same unique ID to the already collected image and the re-taken image. The unique ID is same as that explained in relation to FIG. 11 and will not be explained further. Then a step S1206 displays the re-taken image on the overview 305, whereupon the image re-taking process is terminated.

Figure 13:
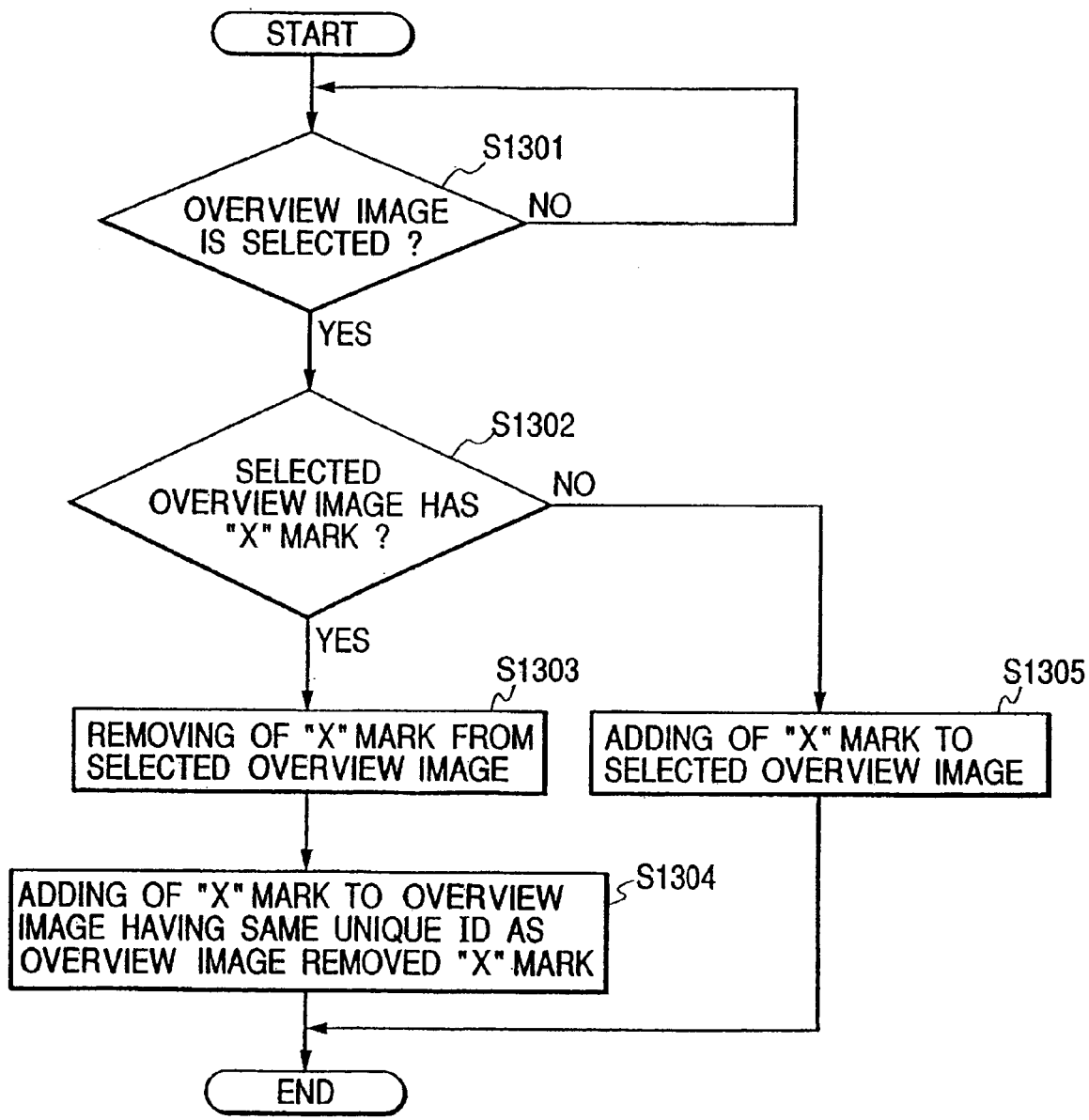
FIG. 13 is a flow chart of an overview image selection process.

FIG. 13 is a flow chart of a process for selecting the overview images, which is to be executed after the image re-taking process according to FIGS. 11 and 12, as will be explained in the following.

A step S1301 discriminates whether any of the overview images 305 as shown in FIG. 4. If selected, a step S1302 discriminates whether a cross mark is present on the selected overview image, and, if present or absent, the sequence respective proceeds to a step S1303 or S1305. A step S1303 displays the selected overview image by detaching the cross mark. A step S1304 searches an image of a unique ID same as that of the overview image from which the cross mark is detached in the step S1303, and attaches a cross mark to the overview image of the same ID. It is thus rendered possible to select only one image without the cross mark among the overview images of a same ID and to transfer the one selected image only to the exterior. In the present embodiment, there is selected only one image, but it is naturally possible also to select and transfer plural images.

A step S1302 identifies that the selected overview image does not bear the cross mark, the sequence proceeds to a step S1305 for attaching a cross mark on the selected overview image.

As explained in the foregoing with reference to FIG. 13, an image suitable for inspection can be selected from a group of images obtained by image re-taking and transferred to the exterior, so that the image re-taking can be executed relatively easily. Also this configuration can flexibly adapt to a situation where the already taken image is found, after the image re-taking, better than the re-taken image.

There is already defined a standard communication protocol called DICOM, which manages the taken images by handling a plurality of taken images as a series, also handling a plurality of the series as a study, and executing the image taking operation in succession in the unit of such study.

Figure 6:
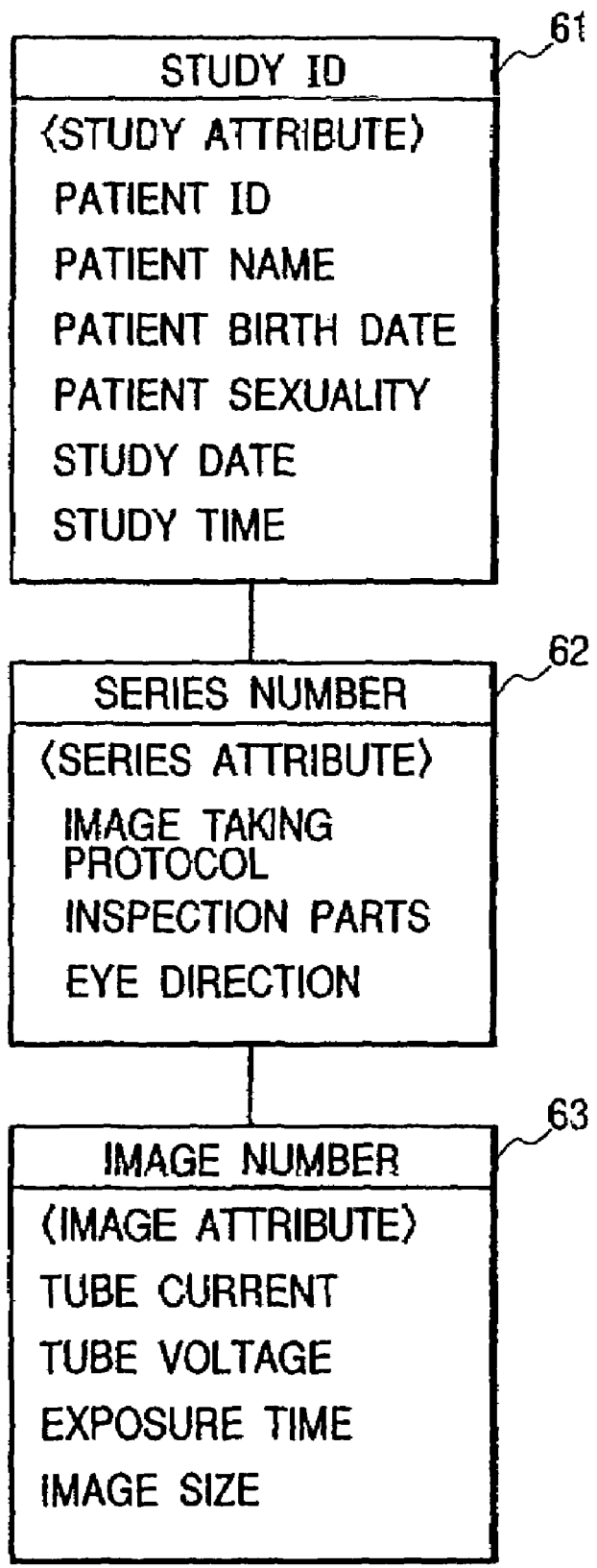
FIG. 6 is a view showing the attributes of a study ID 61, a serial number 62 and an image number 63.

FIG. 6 shows the attributes of a study ID 61, a series number 62 and an image number 63.

Since this protocol is applicable to the inspection of any modality, and is therefore dependent on the condition of preparation of a new series and the condition of image taking condition of the modality. In the digital image collection apparatus of the present embodiment, each image is generally managed as a series.

Figure 7:
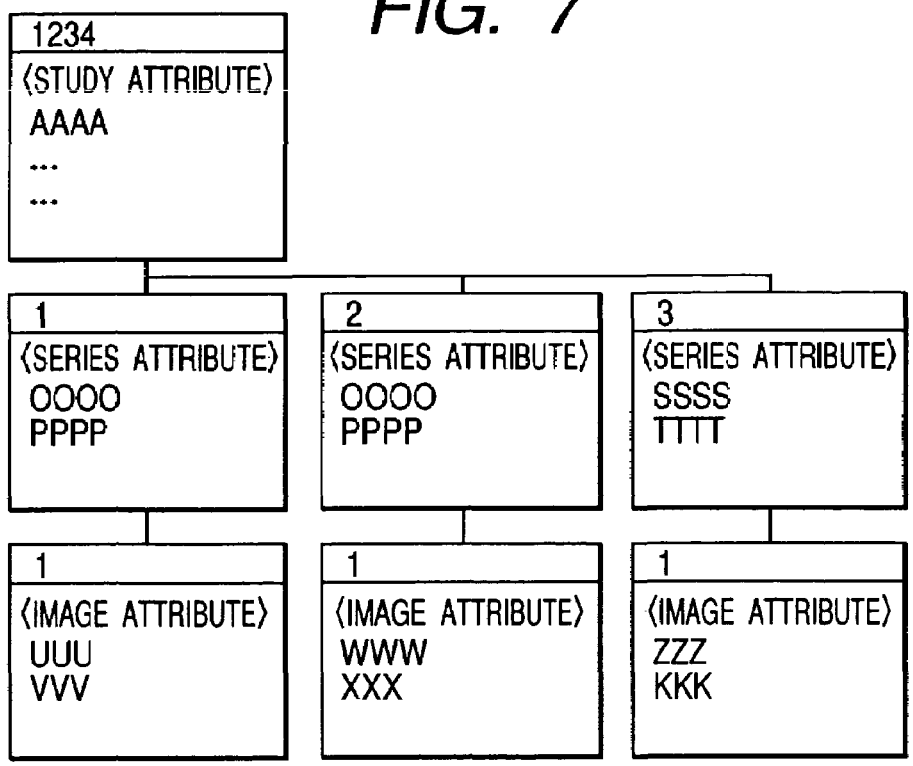
FIG. 7 is a view showing the conventional study attribute, serial attribute and image attribute.

FIG. 7 shows the relationship of the study attribute, series attribute and image attribute in the conventional digital image collection apparatus.

In case a new series is added where a series 1 is already present, there is generated a new series with an assigned series number 2 even if the serial attribute is same, and is attached to a study 1234. In this method, a series is newly assigned when an image is formed in any of all the taken images.

In certain image taking methods, plural images may be taken from a same direction, such as in II-DR still image taking. In such case, there are generated plural images with a same series attribute, so that the serially taken images can be added while fixing the study and the series. The present embodiment can dynamically adapt to such case.

In the following there will be given further explanation with reference to FIG. 8.

Figure 8:
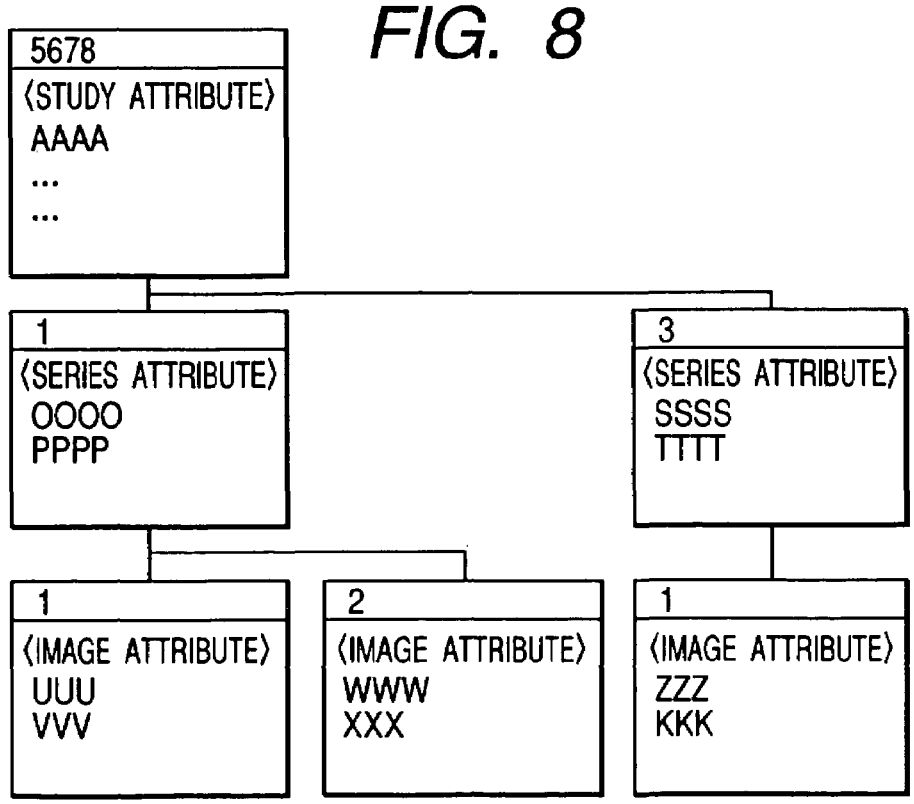
FIG. 8 is a view showing an example of image management in an embodiment of the present invention.

FIG. 8 is a view showing an example of image management in the present embodiment.

At first the image taking operation is executed in a study of an attribute different from that of the past study, there is generated a new study. There is illustrated the generation of a study with the study attribute 5678. The initial image in this study constitutes a new series and a new image, so that a series with the series number 1 is added to the study and a taken image with the image number 1 is added to the series of the series number 1. In FIG. 8, alphabets AAAA, OOOO etc. schematically indicate various attributes.

If a next image taking is executed with the same series attribute, namely with the same image taking protocol, inspected part and viewing direction, the taken image is added with an image number 2 to the series 1.

Then, if a next image taking is executed with at least a different series attribute, namely if any of the image taking protocol, inspected part and viewing direction is made different, a series 2 is newly generated and added to the study of the study number 5678, and the taken image is added as a new image of an image number 1 to the series 2.

The present embodiment is also featured by a fact that the operation can be varied by two modes, in case the image taking is again executed with the attribute of the series 1 after the above-mentioned 3 image takings.

Figure 9:
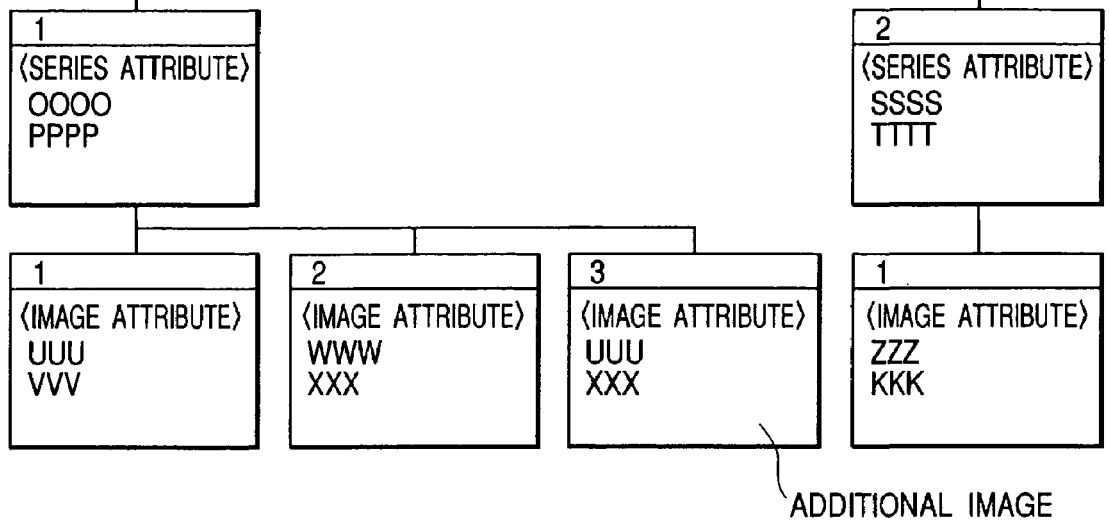
FIG. 9 is a view showing an example of the mode 1.

FIG. 9 shows an example of the mode 1.

This mode searches a past series of the same series attribute, and, if such series is present, adds the taken image to such searched series. In the illustrated example, the taken image is added with an image number 3 to the series of the series number 1.

Figure 10:
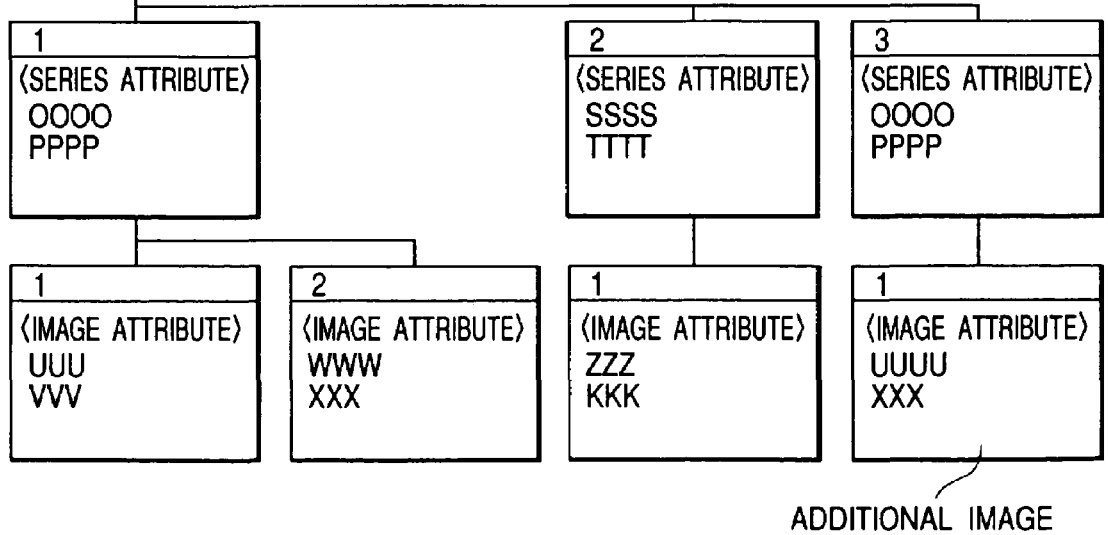
FIG. 10 is a view showing an example of the mode 2.

FIG. 10 shows an example of the mode 2.

This mode does not search the past series of the same series attribute, but generates a new series and adds the taken image thereto. In the illustrated example, the taken image is added with an image number 1 in a new series generated with a series number 3.

Such process is advantageous in the image management, since the serial images of similar attributes can be collectively managed.

In the foregoing embodiment, there has been explained a case of storing the programs in the ROM, but such configuration is not restrictive and there may be employed any arbitrary storage medium. Also there may be adopted a circuit capable of similar functions.

The present invention may be applied to a system consisting of plural equipment or an apparatus consisting of a single equipment. Also the present invention includes a case where a storage medium recording the program codes of a software realizing the functions of the aforementioned embodiments is supplied to a system or an apparatus and the functions of the aforementioned embodiments are realized by reading and executing the program codes stored in the storage medium by a computer (CPU or MPU) of the above-mentioned system or apparatus. In such case the program codes themselves read from the storage medium realize the functions of the aforementioned embodiments, and the storage medium storing the program codes constitutes the present invention.

The storage medium storing such program codes can be, for example, a floppy disk, a hard disk, an optical disk, a magnetooptical disk, a CD-ROM, a CD-R, a magnetic tape, a non-volatile memory card or a ROM.

The present invention also includes such program codes not only in a case where the functions of the aforementioned embodiments are realized by the execution of the read program codes by the computer but also a case where an operating system or the like functioning on the computer executes all or a part of the actual processes under the control of such program codes thereby realizing the functions of the aforementioned embodiments.

The present invention further includes a case wherein the program codes read from the memory medium are once stored in a memory provided in a function expansion board inserted into the computer or a function expansion unit connected to the computer, and a CPU provided in the function expansion board or the function expansion unit executes all the process or a part thereof according to the instructions of such program codes, thereby realizing the functions of the aforementioned embodiments.

As explained in the foregoing, the present invention allows to arbitrarily select the image adapted for inspection from the group of images obtained by image taking.

What is claimed is:

1. An image processing apparatus comprising:
   receiving means for receiving ordering information;
   image taking means for taking an image based on an image taking condition corresponding to the ordering information received by said receiving means;
   storing means for storing the image taken by said image taking means and the image taking condition;
   display control means for controlling display of the image taken by said image taking means;
   selection means for selecting an image as an object for re-taking from among the already-taken images displayed by said display control means;
   re-taking instruction means for instructing said image taking means to re-take the image corresponding to the image selected by said selection means;
   reading means for reading out the image taking condition corresponding to the image selected by said selection means;
   setting means for setting the image taking condition read-out by said reading means to said image taking means;
   re-taking control means for controlling said image taking means to re-take the selected image based on the image taking condition set by said setting means; and
   output means for outputting the re-taking image as the image corresponding to the ordering information.

2. An image processing apparatus according to claim 1, wherein when re-taking of an image is instructed by said re-taking instruction means, said display control means controls to display the image of the object for re-taking and the re-taken image.

3. An image processing apparatus according to claim 2, further comprising output image selection means for selecting an image to be outputted externally from said image processing apparatus from among the images of the object for re-taking and the re-taken image when the image of the object for re-taking and the re-taken image are displayed by said display control means.

4. An image processing apparatus according to claim 1, wherein said display control means controls to display an identification mark for the image not selected by said output image selection means.

5. An image processing apparatus according to claim 1, further comprising attaching means for attaching an image taking ID to the image taken by said image taking means.

6. An image processing apparatus according to claim 5, wherein said attaching means attaches, to the re-taken image, the same image taking ID as the image taking ID attached to the image selected by said selection means, when re-taking is instructed by said re-taking instruction means.

7. An image processing apparatus according to claim 5, wherein the image taking ID includes at least one of a name of an inspected person, a body part whose image is taken, an image taking direction, and an image taking condition.

8. An image processing apparatus comprising:
   image taking means for taking an image;
   storage means for storing the image taken by said image taking means associated with an image taking ID, said storage means being able to store plural images wherein the plural images are able to be associated with a single image taking ID;
   marking means for attaching a mark to one or more images from among the plural images associated with a single image taking ID, the one or more images being images other than the image newly stored by said storage means; and image output means for outputting the image to which the mark is not attached by said marking means as the image corresponding to the single image taking ID.

9. An image processing apparatus according to claim 8, further comprising display control means for controlling to display the taken image having the same image taking ID, when the image is taken by said image taking means in association with the same image taking ID as the image taking ID stored in said storage means.

10. An image processing apparatus according to claim 9, wherein said display control means controls to display the image marked by said marking means.

11. An image processing apparatus according to claim 8, wherein the image taking ID includes at least one of a name of an inspected person, image taking body part, image taking direction, and image taking condition.

12. An image processing method for controlling an image processing apparatus, said method comprising:
   a receiving step, of receiving ordering information;
   an image taking step, of taking an image based on an image taking condition corresponding to the ordering information received in said receiving step;
   a storing step, of storing the image taken in said image taking step and the image taking condition;
   a display control step, of controlling display of the image taken in said image taking step;
   a selection step, of selecting an image as an object for re-taking from among the already-taken images displayed in said display control step;
   a re-taking instruction step, of instructing the image taking apparatus to re-take the image corresponding to the image selected in said selection step;
   a reading step, of reading out the image taking condition corresponding to the image selected in said selection step;
   a setting step, of setting the image taking condition read-out in said reading step for said image taking step;
   a re-taking control step, of controlling said image taking step to re-take the selected image based on the image taking condition set in said setting step; and
   an output step of outputting the re-taking image as the image corresponding to the ordering information.

13. An image processing method according to claim 12, wherein when re-taking of an image is instructed in said re-taking instruction step, said display control step includes controlling to display the image of the object for re-taking and the re-taken image.

14. An image processing method according to claim 13, further comprising an output image selection step, of selecting an image to be outputted externally from the image processing apparatus from among the images of the object for re-taking and the re-taken image when the image of the object for re-taking and the re-taken image are displayed in said display control step.

15. An image processing method according to claim 12, wherein said display control step includes controlling to display an identification mark for the image not selected in said output image selection step.

16. An image processing method according to claim 12, further comprising an attaching step, of attaching an image taking ID to the image taken in said image taking step.

17. An image processing method according to claim 16, wherein said attaching step includes attaching, to the re-taken image, the same image taking ID as the image taking ID attached to the image selected in said selection step, when re-taking is instructed in said re-taking instruction step.

18. An image processing method according to claim 16, wherein the image taking ID includes at least one of a name of an inspected person, a body part whose image is taken, an image taking direction, and an image taking condition.

19. An image processing method for controlling an image processing apparatus, said method comprising:
   an image taking step, of taking an image;
   a storage step, of storing the image taken in said image taking step associated with an image taking ID, said storage step including storing plural images such that the plural images are able to be associated with a single image taking ID;
   a marking step, of attaching a mark to one or more images from among the plural images associated with a single image taking ID, the one or more images being images other than the image newly stored in said storage step; and
   an image output step, of outputting the image to which the mark is not attached in said marking step as the image corresponding to the single image taking ID.

20. An image processing method according to claim 19, further comprising a display control step, of controlling to display the taken image having the same image taking ID, when the image is taken in said image taking step in association with the same image taking ID as the image taking ID stored in said storage step.

21. An image processing method according to claim 20, wherein said display control step controls to display the image marked in said marking step.

22. An image processing method according to claim 19, wherein the image taking ID includes at least one of a name of an inspected person, a body part whose image is taken, an image taking direction, and an image taking condition.

23. A computer-readable storage medium storing a program for executing an image processing method for controlling an image processing apparatus, said program comprising:
   code for a receiving step, of receiving ordering information;
   code for an image taking step, of taking an image based on an image taking condition corresponding to the ordering information received in said receiving step;
   code for a storing step, of storing the image taken in said image taking step and the image taking condition;
   code for a display control step, of controlling display of the image taken in an image taking step in accordance with said code for the image taking step;
   code for a selection step, of selecting an image as an object for re-taking from among the already-taken images displayed in a display control step in accordance with said code for the display control step;
   code for a re-taking instruction step, of instructing re-execution of said code for an image taking step, to re-take an image corresponding to the image selected by execution of said code a selection step;
   code for a reading step, of reading out the image taking condition corresponding to the image selected in said selection step;
   code for a setting step, of setting the image taking condition read-out in said reading step for execution by said code for said image taking step;
   code for a re-taking control step, of controlling said image taking step to re-take the selected image based on the image taking condition set in said setting step; and
   code for an output step, of outputting the re-taking image as the image corresponding to the ordering information.

24. A computer-readable storage medium storing a program for executing an image processing method for controlling an image processing apparatus, said program comprising:
- code for an image taking step, of taking an image;
- code for a storage step, of storing the image taken by execution of said code for an image taking step associated with an image taking ID, said code for a storage step including code for causing storage of plural images such that the plural images are able to be associated with a single image taking ID;
- code for a marking step, of attaching a mark to one or more images from among the plural images associated with a single image taking ID, the one or more images being images other than the image newly stored in said storage step; and
- code for an output step, of outputting the image to which the mark is not attached by execution of said code for an marking step as the image corresponding to the single image taking ID.

25. An image processing apparatus comprising:
- receiving means for receiving ordering information;
- image taking means for taking an image based on an image taking condition corresponding to the ordering information received by said receiving means;
- storing means for storing the image taken by said image taking means and the image taking condition;
- first attachment means for attaching an image taking ID to the image taken by said image taking means;
- display control means for controlling display of the image taken by said image taking means;
- selection means for selecting an image as an object for re-taking from among already-taken images displayed by said display control means;
- re-taking instruction means for instructing said image taking means to re-take an image corresponding to the image selected by said selection means;
- second attachment means for attaching an image taking ID corresponding to the image selected by said selection means to the re-taken image;
- output image selection means for selecting an image to be outputted from among images to which the same taking ID is given;
- reading means for reading out the image taking condition corresponding to the image selected by said selection means;
- setting means for setting the image taking condition read-out by said reading means to said image taking means;
- re-taking control means for controlling said image taking means to re-take the selected image based on the image taking condition set by said setting means; and
- output means for outputting the re-taking image as the image corresponding to the ordering information.

26. An image processing apparatus according to claim 25, wherein said display control means controls to display a mark for an image not selected by said selection means.

27. An image processing apparatus according to claim 25, wherein the image taking ID includes at least one of a name of an inspected person, a body part whose image is taken, an image taking direction, and an image taking condition.

* * * * *

UNITED STATES PATENT AND TRADEMARK OFFICE
CERTIFICATE OF CORRECTION

| | |
|---|---|
| PATENT NO. | : 7,119,841 B2 |
| APPLICATION NO. | : 09/552590 |
| DATED | : October 10, 2006 |
| INVENTOR(S) | : Tsukasa Sako |

It is certified that error appears in the above-identified patent and that said Letters Patent is hereby corrected as shown below:

SHEET 3

FIG. 3, "BLIGHTNESS" should read --BRIGHTNESS--.

SHEET 4

FIG. 4, "BLIGHTNESS" should read --BRIGHTNESS--.

COLUMN 1

Line 52, "frequency" should read --frequently--; and
    Line 60, "despite of" should read --despite--.

COLUMN 4

Line 63, "image" should read --image taking--.

COLUMN 5

Line 6, "condition" should read --operation condition--.

COLUMN 6

Line 47, "depressed" should read --depresses--.

COLUMN 7

Line 58, "305 as shown" should read --305 are selected as shown--; and
    Line 61, "respective" should read --respectively--.

COLUMN 8

Line 25, "and is therefore" should read --it is therefore--.

COLUMN 11

Line 41, "output step" should read --output step,--.

COLUMN 12

Line 56, "code" should read --code for--.

UNITED STATES PATENT AND TRADEMARK OFFICE
CERTIFICATE OF CORRECTION

PATENT NO. : 7,119,841 B2
APPLICATION NO. : 09/552590
DATED : October 10, 2006
INVENTOR(S) : Tsukasa Sako It is certified that error appears in the above-identified patent and that said Letters Patent is hereby corrected as shown below:

<u>COLUMN 13</u>

Line 19, "an marking" should read --a marking--.

Signed and Sealed this

Seventeenth Day of July, 2007

JON W. DUDAS
*Director of the United States Patent and Trademark Office*